United States Patent [19]

Okamoto et al.

[11] 4,280,996

[45] Jul. 28, 1981

[54] FAT EMULSION FOR INTRAVENOUS INJECTION

[75] Inventors: Hiroyuki Okamoto, Akashi; Yoshio Tsuda, Kyoto; Kazumasa Yokoyama, Toyonaka, all of Japan

[73] Assignee: The Green Cross Corporation, Osaka, Japan

[21] Appl. No.: 75,684

[22] Filed: Sep. 13, 1979

[30] Foreign Application Priority Data

May 7, 1979 [JP] Japan .................................. 54-55476

[51] Int. Cl.$^3$ ..................... A61K 31/20; A61K 31/56; A61K 31/685; B01J 13/00
[52] U.S. Cl. ................................. 424/199; 252/316; 424/195; 424/238; 424/318; 424/343
[58] Field of Search ................. 424/199, 19, 195, 238, 424/318, 343; 252/316

[56] References Cited

U.S. PATENT DOCUMENTS

| | | | |
|---|---|---|---|
| 1,939,166 | 12/1933 | Hadjopoulos | 424/199 |
| 2,185,969 | 1/1940 | Schultze | 424/199 |
| 3,004,892 | 10/1961 | Hainsworth et al. | 424/199 |
| 4,089,801 | 5/1978 | Schneider | 252/316 |

FOREIGN PATENT DOCUMENTS

| | | | |
|---|---|---|---|
| 615342 | 2/1961 | Canada | 424/199 |
| 725596 | 1/1966 | Canada | 424/199 |
| 8014M | 7/1970 | France | 424/199 |

OTHER PUBLICATIONS

Martindale-The Extra Pharmacopoeia-27th ed. (1977) -The Pharmaceutical Press, London-pp. 1034–1035.
Biochem. & Biophysical. Res. Commn. 72 (4) (1976) 1251–1258, Krupp et al.
ACTA-Academiae Aboensis, Ser. B. 34(7) pp. 1–10 (1974), Lundberg et al.

*Primary Examiner*—Douglas W. Robinson
*Attorney, Agent, or Firm*—Cushman, Darby & Cushman

[57] ABSTRACT

A stable fat emulsion having low side effects, which is suitable as nutritive infusion fluid for intravenous injection, is provided. The emulsion contains 5–50 (W/V) % of soybean oil, yolk phospholipids in a weight ratio to the soybean oil of $\frac{1}{4}$–1/25, 0.01–0.30 (W/V) % of a fatty acid or salt thereof having 12–20 carbon atoms and the balance of water.

4 Claims, No Drawings

FAT EMULSION FOR INTRAVENOUS INJECTION

This invention relates to a nutritive infusion fluid and, more particularly, to a fat emulsion for intravenous injection.

In preparing conventional fat emulsions, there have been used emulsifiers such as nonionic surface active agents, yolk phospholipids and soybean phospholipids. The properties of an emulsion naturally vary with the type of emulsifier or of emulsifying aid being used. Since the emulsion, as herein referred to, is a nutritive infusion fluid, it is desirable that the emulsion is used up rapidly in vivo as an energy source after administration. In order that the intravenously injected fat may be rapidly consumed by combustion in the body, it is necessary that the fat does not remain for long periods in blood and that the fat is metabolized without deposition and accumulation in tissues and organs such as the liver and spleen.

For the above reasons, it is necessary to develop an emulsion in which the particles are fine and stable. The present inventors found that by the addition of several emulsifiers and emulsifying aids to a conventional fat emulsion for intravenous injection containing soybean oil, water and yolk phospholipids and by subsequent homogenizing it is possible to prepare a fat emulsion which, as compared with known emulsions, has far finer particles, and is far stable and more rapidly utilized as energy source in vivo. Based on this finding, the present invention has been accomplished.

According to this invention, there is provided a fat emulsion for intravenous injection comprising 5 to 50 (W/V)% of soybean oil, yolk phospholipids at a weight ratio to the soybean oil of ¼ to 1/25, 0.01 to 0.30 (W/V)% of a fatty acid having 12 to 20 carbon atoms or a pharmaceutically acceptable salt thereof, 0.005 to 0.50 (W/V)% of a cholesterol and the balance of water; (W/V)% being the percentage of the weight of a solute or dispersed phase in unit volume of the emulsion.

The soybean oil to be used in preparing the infusion fluid of this invention is a highly purified soybean oil prepared, for example, by the steam distillation method [H. J. Lips, J. Am Oil Chemist. Soc., 27, 422–423 (1950)] from refined soybean oil, the purity of said highly purified soybean oil being 99.9% or more in terms of the triglyceride, diglyceride and monoglyceride content. Although not subject to particular limitation, the weight ratio of soybean oil to water is generally 0.05 to 0.43, preferably 0.05 to 0.2.

The purified yolk phospholipides used in this invention can be prepared by the usual fractionation with an organic solvent in the following way: To a solution of 130 g of crude yolk phospholipids in a cold mixture of 200 ml of n-hexane and 100 ml of acetone, is added gradually with stirring 1,170 ml of cold acetone. The insolubles are collected by filtration and again dissolved in a cold mixture of 260 ml of n-hexane and 130 ml of acetone. To the stirred solution, is added 1,170 ml of cold acetone. The insolubles are collected by filtration and freed from the solvent by evaporation to obtain 60 g of a dried substance containing 70–80% of phosphatidylcholine, 12–25% of phosphatidylethanolamine, and other phospholipids including phosphatidylinositol, phosphatidylserine, sphingomyelin and lyzophosphatidylcholine [D. J. Hanahan et al., J. Biol. Chem., 192, 623–628 (1951)].

The fatty acids to be used can be those free fatty acids having 12 to 20 carbon atoms which are usable as medicines or pharmaceutically acceptable salts thereof. Examples are stearic acid, oleic acid, linoleic acid, palmitic acid, linolenic acid, and potassium or sodium salts thereof. The amount to be used is 0.01 to 0.30, preferably 0.04 to 0.07 (W/V)% as a final concentration in the emulsion. The cholesterols can be those which are suitable for the medical treatment by intravenous injection. The amount to be added is 0.05 to 0.005 (W/V)% as a final concentration in the emulsion.

In preparing the emulsion of this invention, the homogenizing can be performed in a customary way by means of ultrasonic treatment or pressure atomization. The intended emulsion is obtained, for example, by passing the fluid composition 10 times through a Manton-Gaulin homogenizer under application of a pressure of 500 kg/cm$^2$ [R. P. Geyer et al., J. Am. Oil Chem. Soc., 32, 365–370 (1955)]. The emulsion of this invention can contain glycerol or glucose to make it isotonic.

As compared with conventional fat emulsions in which soybean phospholipids, nonionic surface active agents, and yolk phospholipids are used as emulsifiers, the fat emulsion for intravenous injection according to this invention is superior in physicochemical stability and in lower side effects. The emulsion of this invention contains dispersed oil droplets having an average diameter of $0.1\mu$ or less, none of the particles has a diameter exceeding $1\mu$, and the state of fine dispersion remains unchanged for a long period of time.

The fat emulsion of this invention showed $LD_{50}$ in rats of 200 ml or more per kg of body weight for a 10% fat emulsion and 150 ml or more for a 20% fat emulsion. No hemolisis is observed on instillation at a normal rate.

Instruction for use of the present preparation: A dose of 300 to 1,000 ml of a 10% of fat emulsion is administered once a day by intravenous drip. The dose is suitably adjusted in accordance with the body weight and the symptom; and the amount of fat administered intravenously is 2 g (20 ml of the emulsion) or less per day per kg of the body weight.

The invention is illustrated below in detail with reference to Examples and Experimental Examples.

EXAMPLE 1

To 20.0 g of purified soybean oil, were added 2.4 g of purified yolk phospholipids, 0.05 g of sodium oleate and 0.04 g of cholesterol. The mixture was heated at 65° to 75° C. to form a solution. To the solution were added 5.0 g of glycerol and 173 ml of distilled water for injection which had been heated at 65° to 75° C. The resulting mixture was coarsely emulsified by means of a Homomixer. The coarse emulsion was finely emulsified by passing 10 times through a Manton-Gaulin homogenizer under a first stage pressure of 120 kg/cm$^2$ and a total pressure of 500 kg/cm$^2$ to obtain a homogenized and very finely dispersed fat emulsion.

EXAMPLE 2

To 40.0 g of purified soybean oil, were added 2.4 g of purified yolk phospholipids, 0.05 g of sodium oleate and 0.04 g of cholesterol. The mixture was heated at 65° to 75° C. to form a solution. To the solution were added 5.0 g of glycerol and 173 ml of distilled water for injection which had been heated at 65° to 75° C. The resulting mixture was coarsely emulsified by means of a Homomixer. The coarse emulsion was finely emulsified by passing 10 times through a Manton-Gaulin homogenizer under a first stage pressure of 120 kg/cm$^2$ and a total pressure of 500 kg/cm$^2$ to obtain a uniform and finely dispersed fat emultion.

EXPERIMENTAL EXAMPLE 1

A comparative experiment was conducted on the stability of emulsion in relation to the composition of emulsifier. Emulsion samples were prepared in a manner similar to that in Example 1, using four emulsifier systems comprising purified yolk phospholipids alone, a combination of purified yolk phospholipids and cholesterol or a free fatty acid, or a combination (according to this invention) of purified yolk phospholipids, cholesterol and a free fatty acid.

The particle size of each emulsion sample was measured by means of an electron microscope immediately after the preparation and after the storage for 24 months at 4° C. The electron microscope used was model JEM-T$_s$7 of Nippon Denshi Co. The average particle diameter was determined by measuring the particle size from the photograph taken by the carbon replica technique. It was found that the emulsion prepared by using an emulsifier system comprising purified yolk phospholipids, a free fatty acid and cholesterol had uniform and fine particles which remained stable without significant deterioration for a long period of time, indicating that this emulsion is the most excellent of the four emulsions (Table 1).

TABLE 1

Particle diameter of emulsion and stability for storage

| Sample No. | Emulsifier | Particle dia. of fat emulsion ($\mu$) | Particle dia. after storage for 24 months at 4° C. ($\mu$) |
|---|---|---|---|
| I | Purified yolk phospholipids | 0.15 ± 0.03 | 0.25 ± 0.06 |
| II | Purified yolk phospholipid and cholesterol | 0.13 ± 0.03 | 0.20 ± 0.03 |
| III | Purified yolk phospholipid and fatty acid | 0.09 ± 0.02 | 0.13 ± 0.03 |
| IV | Purified yolk phospholipids, cholesterol and fatty acid (this invention) | 0.08 ± 0.02 | 0.11 ± 0.03 |

EXPERIMENTAL EXAMPLE 2

Four fat emulsions were prepared in the same manner as in Experimental Example 1, except that soybean oil having $^{14}C$ labelled linolic acid in the structure was used. Four groups of Wistar-strain male rats (each 150 g in body weight), which had been fasted for 16 hours, were administered through tail vein with the above emulsions, respectively, at a dose of 20 ml (2 g as soybean oil) per kg of body weight. After the injection, the expiratory air of each rat was collected continually for 6 hours and the radioactivety was measured to compare the emulsions with one another for the metabolic rate of fat as energy source. After the above experiment, each rat was sacrificed and subjected to laparotomy to determine the remaining radioactivity in the plasma, liver, spleen and lung.

Further, the emulsions were injected into tail vein of rats in the same manner as mentioned above. Blood samples were collected from the eyeground of each rat after 10, 15, 20, 30, 60, 90, 120 and 180 minutes from the injection. The neutral fat content of the plasma separated by centrifugation was measured by the acetylacetone method to determine the half-life (T$\frac{1}{2}$) of neutral fat in the plasma. The results obtained were as shown in Table 2.

TABLE 2

| Sample No. | Half-life (T$\frac{1}{2}$) in plasma (minute) | Recovered radioactivity in expired air during 6 hours after administration (% based on dose) | Distribution of radioactivity after 6 hours from administration | | | |
|---|---|---|---|---|---|---|
| | | | Plasma | Liver | Spleen | Lung |
| I | 18.5 | 20.1 ± 2.5* | 0.4 ± 0.05* | 46.1 ± 6.4* | 5.2 ± 1.0* | 2.3 ± 0.1 |
| II | 28.3 | 25.3 ± 2.1 | 1.3 ± 0.2 | 31.5 ± 2.8 | 2.4 ± 0.4 | 1.8 ± 0.2 |
| III | 34.4 | 27.6 ± 3.1 | 1.6 ± 0.2 | 30.1 ± 5.8 | 1.8 ± 0.3 | 1.5 ± 0.1 |
| IV | 35.2 | 29.7 ± 2.6 | 1.5 ± 0.1 | 33.6 ± 4.9 | 2.2 ± 0.5 | 1.8 ± 0.03 |

Note:
*Significant difference from the values of IV.

As described in the foregoing, it is apparent that as compared with the fat emulsion in which purified yolk phospholipids were used as a sole emulsifier, the fat emulsion prepared by using a free fatty acid and cholesterol as emulsifying aids coincidently with yolk phospholipids contains more finely dispersed particles, which remain uniform for a long period of time, and is utilized more rapidly as energy source in vito, indicating that in this respect the emulsion of this invention is superior to conventional fat emulsions.

What is claimed is:

1. A fat emulsion suitable for intravenous injection comprising 5 to 50 (w/v)% of soybean oil, yolk phospholipids in a weight ratio of the soybean oil of $\frac{1}{4}$ to 1/25, glycerol or glucose as an isotonic agent, the diameter of the emulsified particles being 0.1$\mu$ or less, water, 0.01 to 0.30 (w/v)% of a fatty acid having 12 to 20 carbon atoms or a pharmaceutically acceptable salt thereof and 0.005 to 0.50 (w/v)% of cholesterol.

2. An emulsion according to claim 1, wherein the amount of the fatty acid or pharmaceutically acceptable salt thereof is 0.04 to 0.07 (W/V)%.

3. An emulsion according to 1 wherein the fatty acid is stearic acid, oleic acid, linoleic acid, palmitic acid or linolenic acid and the amount of the fatty acid or pharmaceutically acceptable salt thereof is 0.04 to 0.07 (w/v)%.

4. An emulsion according to claim 1 which is characterized by being sufficiently stable after storage at 4° C. for 24 months that the emulsified particles have a diameter of not over 0.11±0.03$\mu$.

* * * * *